ary Examiner—Joseph Paul Brust

United States Patent [19]

Cook et al.

[11] Patent Number: 4,959,385

[45] Date of Patent: Sep. 25, 1990

[54] THIOFORMAMIDE DERIVATIVES

[75] Inventors: David C. Cook, London; Terance W. Hart, Brentwood; Iain M. McLay, Loughton; Malcolm N. Palfreyman, Upminster; Roger J. Walsh, Rayleigh, all of England; Jean-Claude Aloup, Villeneuve-le-Roi, France

[73] Assignee: May & Baker Limited, Dagenham, England

[21] Appl. No.: 299,039

[22] Filed: Jan. 19, 1989

[30] Foreign Application Priority Data

Jan. 21, 1988 [GB] United Kingdom ............... 8801300

[51] Int. Cl.$^5$ ............... A61K 31/38; C07D 333/20; C07D 335/02; C07D 337/04
[52] U.S. Cl. ............... 514/431; 514/432; 514/446; 514/448; 549/9; 549/13; 549/28; 549/72
[58] Field of Search ............... 549/9, 13, 28, 72; 514/431, 432, 446, 448

[56] References Cited

U.S. PATENT DOCUMENTS 3,206,473  9/1965  Faith ............... 549/79

Primary Examiner—Joseph Paul Brust
Assistant Examiner—M. S. Howard
Attorney, Agent, or Firm—Stevens, Davis, Miller & Mosher

[57] ABSTRACT

This invention relates to thioformamide derivatives of the formula:

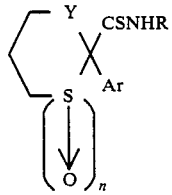

wherein R represents alkyl, Ar represents optionally substituted phenyl, Y represents an ethylene or methylene radical or a valency bond, and n represents 0 or 1, bioprecursors thereof and pharmaceutically acceptable salts thereof which possess useful pharmacological properties, processes for their preparation and compositions containing them.

8 Claims, No Drawings

THIOFORMAMIDE DERIVATIVES

This invention relates to new therapeutically useful thioformamide derivatives, to processes for their preparation and to pharmaceutical compositions containing them.

The new thioformamide derivatives of the present invention are those compounds of the general formula (I) hereinafter depicted, wherein R represents a straight- or branched-chain alkyl radical containing from 1 to 4 carbon atoms, preferably methyl, Ar represents an optionally substituted phenyl group, Y represents a valency bond or an ethylene or preferably methylene radical, and n represents 0 or preferably the integer 1, pharmaceutically acceptable bioprecursors thereof and pharmaceutically acceptable salts thereof.

The group Ar is preferably substituted in the 3 and-/or 5 position with an electron-withdrawing group for example a cyano, nitro, trifluoromethyl, carbamoyl, carboxy, $C_{2-5}$-alkanoyl, $C_{2-5}$-alkoxycarbonyl or $C_{1-4}$-alkylsulphonyl group or a fluorine, chlorine or bromine atom, and optionally further substituted with halogen atom(s), $C_{1-4}$-alkyl or $C_{6-12}$-aryl (e.g. phenyl) group(s), or the group Ar may be substituted with halogen atom (s), $C_{1-4}$-alkyl or $C_{6-12}$-aryl (e.g. phenyl) group(s) or with substituents which together form a fused ring, for example a 2-naphthyl group.

The group Ar may represent, for example, the phenyl, 4-chlorophenyl, 4-phenylphenyl, 3-trifluoromethylphenyl, 3-fluorophenyl, 3-cyanophenyl, 3-carbamoylphenyl, 3,4-dichlorophenyl, 3,5-dichlorophenyl or 2-naphthyl group.

The presence of an oxygen atom on the ring sulphur atom creates an asymmetry in the molecule which, in association with the adjacent asymmetric carbon atom, leads to 4 stereoisomers which, optionally, can be separated into 2 racemic pairs. The racemic pair and its enantiomers of the general formula (II) in which R, Ar and Y are as hereinbefore defined, i.e. the compounds in which the oxygen atom of the sulphoxide group is in the trans position relative to the group —CSNHR are preferred. Furthermore, in certain cases the substituents R contribute to stereoisomerism. All such forms are embraced by the present invention.

The compounds of general formula (I) in which n represents 0 are transformed in vivo to the corresponding compounds of general formula (I) in which n represents 1, and are therefore preferred bioprecursors.

By the expression "pharmaceutically acceptable bioprecursor" as used in this specification is meant a compound which is converted in vivo into a compound of general formula (I).

Preferred compounds of general formula (I) are as follows:

A (±)-trans-N-methyl-2-phenyltetrahydrothiopyran-2-carbothioamide-1-oxide

B (±)-trans-2-(4-chlorophenyl)-N-methyltetrahydrothiopyran-2-carbothioamide-1-oxide C (±)-trans-N-methyl-2-(3-trifluoromethylphenyl)-tetrahydrothiopyran-2-carbothioamide-1-oxide D (±)-trans-N-methyl-2-(2-naphthyl)tetrahydrothiopyran-2-carbothioamide-1-oxide E (±)-trans-2-(3,4-dichlorophenyl)-N-methyltetrahydrothiopyran-2-carbothioamide-1-oxide F (±)-trans-N-methyl-2-(4-phenylphenyl)tetrahydrothiopyran-2-carbothioamide-1-oxide G (±)-trans-2-(3-cyanophenyl)-N-methyltetrahydrothiopyran-2-carbothioamide-1-oxide H (±)-2-(3,4-dichlorophenyl)-N-methyltetrahydrothiopyran-2-carbothioamide I (±)-trans-2-(3-carbamoylphenyl)-N-methyltetrahydrothiopyran-2-carbothioamide-1-oxide J (±)-N-methyl-2-phenyltetrahydrothiophene-2-carbothioamide-1-oxide K (±)-N-methyl-2-phenyltetrahydrothiophene-2-carbothioamide-1-oxide L (±)-trans-2-(3-fluorophenyl)-N-methyltetrahydrothiopyran-2-carbothioamide-1-oxide M (±)-trans-2-(3,5-dichlorophenyl)-N-methyltetrahydrothiopyran-2-carbothioamide-1-oxide as well as their enantiomeric and diastereoisomeric forms.

The letters A to M are allocated to the compounds for easy reference later in the specification, e.g. in the Table and in the Examples.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; irritable bladder syndrome; and premature labour.

For example, compounds of general formula (I) were submitted to:

Vaso-relaxant Activity Tests.

The test methods used were adapted from those described by Winslow et al [Eur. J. Pharmacol., 131, 219–228 (1986)] and Karaki [J. Pharmacol. Methods, 18, 21 (1987)]for differentiating vaso-relaxant activity. Test A : Activity against contractions induced by low $K^+$ concentrations in the isolated rat aorta Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the test compound which reduced the $K^+$-induced contraction by 90% was determined and expressed in $\mu M$ as the effective concentration ($EC_{90}$), given in Table I.

Test B: Activity against contractions induced by high $K^+$ concentrations in isolated rat aorta The test method was as in Test A except that contractions were induced by addition of 60 mM $K^+$ to the bathing solution. The cumulative addition of solutions of the test compound was conducted and the concentration in the bath reducing the $K^+$-induced contraction by 90% was greater than 30 $\mu M$ for Compounds C and G, and much greater than 30 $\mu M$ for Compounds A, B, E and I.

TABLE I

| Compound | Activity Test A EC$_{90}$ μM |
| --- | --- |
| A | 9.5 |
| B | 2.8 |
| C | 0.8 |
| E | 0.3 |
| G | 1.6 |
| I | 12 |

The compounds of general formula (I) can be prepared by the application or adaptation of known methods, for example as hereinafter identified. By the term "known methods" as used in this specification is meant methods heretofore used or described in the literature.

According to a feature of the present invention, the compounds of general formula (I) may be prepared by the reaction of a compound of general formula (III) wherein Ar, Y and n are as hereinbefore defined with an inorganic base such as sodamide or an organic base such as potassium tert. butoxide or preferably an organolithium derivative followed by reacting the resulting compound with an isothiocyanate of the general formula (IV)

$$R-N=C=S \qquad (IV)$$

wherein R represents a straight-or branched-chain alkyl radical containing 1 to 4 carbon atoms.

The organo-lithium derivatives which are particularly suitable are preferably alkyllithium compounds, such as butyllithium and isopropyllithium, or phenyllithium, dissolved in an inert organic solvent such as hexane, or lithium amides, such as lithium diethylamide or lithium diisopropylamide.

The reaction is generally carried out in an anhydrous inert organic solvent such as tetrahydrofuran or hexamethylphosphoramide, or a mixture of these solvents, at a temperature from −80° C. to 0° C., preferably in an inert atmosphere.

According to a feature of the present invention, the compounds of general formula (I) wherein n represents 0 may be prepared by the reduction of a compound of general formula (I) wherein n represents 1.

The reduction is generally carried out in an anhydrous inert organic solvent such as methylene chloride at a temperature from −20° C. to +50° C., using phosphorus pentasulphide.

According to a feature of the present invention, the compounds of general formula(II) may be prepared by the electrochemical oxidation of the ring sulphur atom of a compound of general formula (I) wherein n represents 0, the oxidation being carried out in an electrolyte with a high water content, at a pH from 7 to 7.5 and in the presence of a specific oxidising agent X$^+$ obtained in situ from a halide X$^-$, by an electrochemical method, and at an imposed electrode potential close to the oxidation potential of X$^-$, in a similar manner to that described in European Patent Publication No. 135638.

In order to produce the oxidising agent X$^+$, one may use an alkali metal iodide such as potassium iodide, or an ammonium halide such as ammonium iodide, triethyl-n-propylammonium iodide or tetraethylammonium bromide, or an aryl iodide such as phenyl iodide, the reaction being carried out at an imposed electrode potential from 0.6 to 0.8V relative to a saturated calomel reference electrode.

The electrolyte in which the oxidation is carried out generally consists of:
- an organic solvent miscible with water capable of dissolving the sulphide of general formula (I) to be oxidised, such as acetonitrile or an alcohol, e.g. methanol or ethanol,
- distilled or deionised water, and
- an aqueous buffer solution at pH 7, generally consisting of a mixture of 0.1M aqueous solutions of ammonium hydrogenphosphate and ammonium dihydrogenphosphate.

The relative proportions of water and organic solvent depend on the solubility in water of the sulphide of general formula (I) to be oxidised. The total percentage of water in the electrolyte can vary from 10 to 99%; it is preferably from 40% to 80% by volume.

According to a feature of the invention, the thioformamide derivatives of general formula (I) may be prepared by the process which comprises reacting an amine of the general formula:

$$R\text{-}NH_2 \qquad (V)$$

(wherein R is as hereinbefore defined) with a dithioester of the general formula (VI) wherein the symbols Ar, Y and n are as hereinbefore defined, and R' represents a straight-or branched-chain alkyl radical containing 1 to 4 carbon atoms, or a benzyl or carboxymethyl radical.

In general, the reaction is carried out with an excess of an amine of general formula (V), without a solvent or in an organic solvent such as an aromatic hydrocarbon, an ether or an alcohol of low molecular weight, or a mixture of these solvents, at a temperature from 20° to 130° C., optionally under pressure.

It is particularly advantageous for the thiol formed during the reaction to be fixed in the form of a heavy metal salt using a thiol acceptor such as mercuric chloride.

The dithioester of general formula (VI) can be obtained by the following methods:

(1) By reaction of a strong base with a heterocyclic compound of the general formula (III) (wherein Ar, Y and n are as hereinbefore defined), followed by reacting the resulting product with carbon disulphide and then with a compound of the general formula:

$$R'\text{---}Z \qquad (VII)$$

wherein R' is as hereinbefore defined, and Z represents a halogen atom, preferably a chlorine, bromine or iodine atom, or a reactive ester radical, preferably a mesyloxy or tosyloxy radical.

The reaction is generally carried out in an ether such as tetrahydrofuran, to which hexamethylphosphoramide has generally been added, at a temperature from −20° to +50° C.

It is particularly advantageous to employ potassium tert.-butoxide as the strong base.

Alternatively the organo-lithium derivatives described above may be employed.

The heterocyclic compounds of general formula (III) can be prepared by one of the following methods: (a) By the cyclisation of a compound of the general formula:

$$\text{Ar-CH}_2\text{S(O)}_n(\text{CH}_2)_m X \qquad (VIII)$$

wherein Ar and n are as hereinbefore defined, m represents 3, 4 or 5 and X represents a halogen atom, preferably a chlorine or bromine atom, or a reactive ester radical, preferably a mesyloxy or tosyloxy radical.

The reaction is generally carried out in an anhydrous organic solvent such as tetrahydrofuran or hexamethylphosphoramide, or a mixture of these solvents, at a temperature from $-20°$ to $+50°$ C., in the presence of an organic base such as potassium tert.-butoxide.

In practice, it is possible to prepare the dithioester of general formula (VI) from the compound of the general formula (VIII) without isolating the compound of the general formula (III). In this case, the compound of the general formula (VIII) is cyclised under the conditions indicated above, at least two equivalents of organolithium derivative being used, and the carbon disulphide and the compound of general formula (VII) are then added to the reaction mixture following the procedure indicated above.

The compounds of general formula (VIII) where $n=1$ can be obtained by oxidising a sulphide of the general formula (VIII) wherein Ar, m and X are as hereinbefore defined and $n=0$.

The oxidation is carried out using one equivalent of a reagent used for converting a sulphide to a sulphoxide, the reaction being carried out in a suitable solvent. For example, it is possible to use hydrogen peroxide in acetone or in acetic acid, an alkali metal periodate in an aqueousorganic solvent such as water/ethanol or water/acetonitrile, acetonitrile, or a peroxycarboxylic acid (e.g. peracetic, perbenzoic, m-chloroperbenzoic, p-nitroperbenzoic or perphthalic acid) in a chlorinated solvent (e.g. methylene chloride or dichloroethane), in acetic acid or in a mixture of these solvents. The reaction is generally carried out at a temperature from $-10°$ to $+30°$ C.

In practice, it is particularly advantageous to use m-chloroperbenzoic acid, the reaction being carried out in methylene chloride at a temperature of about 0° C.
(b) By the oxidation of a compound of the general formula (III) where $n=0$.

The oxidation is carried out under the conditions described above for the preparation of the compounds of the general formula (VIII) where $n=1$.

Alternatively the dithioester of general formula (VI) where $n=1$ can be obtained:

(2) By the oxidation of a dithioester of the general formula (VI) where $n=0$.

The oxidation of the dithioesters of general formula (VI) where $n=0$ can be carried out under the conditions described above for the preparation of compounds of general formula (VIII) where $n=1$.

The dithioester compounds of general formula (VI) where $n=1$ obtained by processes (1) and (2) described above can be used either directly in the form of a mixture of the diastereoisomeric forms, or after separation of these forms (e.g. by fractional crystallisation or chromatography).

It will be understood that it may be desirable to change one or more of the substituents at an appropriate stage during the synthesis of the compounds of the invention, for example, the compounds of general formula (I) wherein Ar represents a phenyl group substituted by a carbamoyl group may be alternatively prepared from the corresponding compounds of general formula (I) wherein Ar represents a phenyl group substituted by a cyano group by the application or adaptation of known methods for such conversion.

The thioformamide derivatives of general formula I obtained by the aforedescribed processes can be purified by the usual physical methods, in particular crystallisation and chromatography, especially to resolve mixtures of enantiomers using a chiral column.

Compounds of general formula (VIII) may be prepared by known methods.

By the term "pharmaceutically acceptable salts" as used in this specification is meant salts the cations of which are relatively innocuous to the animal organism when used in therapeutic doses so that the beneficial pharmaceutical properties of the parent compounds of general formula (I) capable of forming salts are not vitiated by side-effects ascribable to those cations.

The following Examples illustrate the preparation of compounds according to the present invention.

EXAMPLE 1

Compound A

A stirred solution of diisopropylamine (2.15 g) in anhydrous tetrahydrofuran (50 ml), under argon, was cooled to $-60°$ C., and treated with a solution of butyllithium in hexane (1.6M, 13.84 ml). The solution was allowed to warm to 20° C., stirred at this temperature for 10 minutes, then cooled to $-60°$ C. The solution was treated dropwise during 5 minutes at $-60°$ C., with a solution of ($\pm$)-2-phenyltetrahydrothiopyran-1-oxide (mixture of cis/trans isomers)(3.36 g) in anhydrous tetrahydrofuran (35 ml) and stirring was continued for 15 minutes at $-60°$ C. The resulting yellow solution was treated dropwise during 5 minutes, at $-60°$ C., with a solution of methyl isothiocyanate (1.62 g) in anhydrous tetrahydrofuran (25 ml) and stirring was continued for 2 hours at $-60°$ C.

The reaction mixture was treated with water (45 ml) and ethyl acetate (45 ml), allowed to warm to 0° C. and kept at this temperature for 18 hours during which time a colourless solid crystallised. This solid was separated by filtration and recrystallised from ethanol to give ($\pm$)-trans-N-methyl-2-phenyltetrahydrothiopyran-2-carbothioamide-1-oxide, colourless crystals (1.25 g), melting point 241°–243° C.

EXAMPLE 2

Compounds B to F

A solution of ($\pm$)-2-(4-chlorophenyl)tetrahydrothiopyran-1-oxide (mixture of cis/trans isomers) (3.42 g) in anhydrous tetrahydrofuran (40 ml), under argon, was treated dropwise during 5 minutes at -60° C. with a solution of butyllithium in hexane (1.6M, 9.38 ml). Stirred for 30 minutes at $-60°$ C. and then treated at this temperature with a solution of methyl isothiocyanate (1.10 g) in anhydrous tetrahydrofuran (20 ml). The reaction mixture was allowed to warm to 0° C. and stirred for 2 hours at this temperature.

The reaction mixture was treated with water (20 ml) and ethyl acetate (15 ml). The organic layer was separated, dried over magnesium sulphate and evaporated. The residual buff solid was triturated with toluene to give ($\pm$)-trans-2-(4-chlorophenyl)-N-methyltetrahydrothiopyran-2-carbothioamide-1-oxide, a colourless solid (0.77 g), melting point 238°–239° C.

By proceeding in a similar manner to that hereinbefore described above but replacing ($\pm$)-2-(4-chlorophenyl)tetrahydrothiopyran(mixture of cis/trans isomers) by the appropriate tetrahydrothiopyran-1-oxide, there were prepared:

(±)-trans-N-methyl-2-(3-trifluoromethylphenyl)tetrahydrothiopyran-2-carbothioamide-1oxide, a colourless solid, melting point 210°–212° C., after being purified by trituration with ethyl acetate from (±)-2-(3-trifluoromethylphenyl)tetrahydrothiopyran-1oxide (mixture of cis/trans isomers).

(±)-trans-N-methyl-2-(2-naphthyl)tetrahydrothiopyran-2-carbothioamide-1-oxide, a colourless solid, melting point 240°–242° C., after being purified by trituration with toluene from (±)-2-(2-naphthyl)tetrahydrothiopyran-1-oxide (mixture of cis/trans isomers).

(±)-trans-2-(3,4-dichlorophenyl)-N-methyltetrahydrothiopyran-2-carbothioamide-1-oxide, a colourless solid, melting point 239°–240° C., after being triturated with toluene from (±)-2-(3,4-dichlorophenyl)tetrahydrothiopyran-1-oxide (mixture of cis/trans isomers).

(±)-trans-N-methyl-2-(4-phenylphenyl)tetrahydrothiopyran-2-carbothioamide-1-oxide, as colourless crystals, melting point 235°–236° C., after being triturated with acetone and recrystallised from ethanol/dimethylformamide, from (±)-2-(4-phenylphenyl)tetrahydrothiopyran-1-oxide (mixture of cis/trans isomers). The reaction mixture was worked up by treating with water (200 ml) and extracting with methylene chloride (2×200 ml). The combined extracts were dried over magnesium sulphate and evaporated.

EXAMPLE 3

Compound G

A solution of (±)-2-(3-cyanophenyl)tetrahydrothiopyran-1-oxide (mixture of cis/trans isomers)(2 g) in anhydrous tetrahydrofuran (60 ml) and hexamethylphosphoramide (20 ml), under argon, was treated dropwise at 75° C. with a solution of butyl lithium in hexane (1.6M,. 7.32 ml). The resulting dark red/brown solution was stirred for a further 1 hour at −75° C. before the dropwise addition of a solution of methyl isothiocyanate (0.84 g) in anhydrous tetrahydrofuran (20 ml) at −60° C. The reaction mixture was allowed to warm to ambient temperature and stirred for 18 hours at this temperature.

The reaction mixture was treated with saturated saline solution (20 ml) and the layers separated. The aqueous layer was extracted with ethyl acetate (50 ml) and the combined organic layers washed with saturated saline solution (50 ml), dried over magnesium sulphate and concentrated in vacuo to give a dark brown oil. The oil was subjected to medium pressure liquid chromatography using 5% methanol in ethyl acetate as eluent. The resulting (±)-trans-2-(3-cyanophenyl)N-methyltetrahydrothiopyran-2-carbothioamide-1-oxide was recrystallised from isopropanol to give a cream solid (0.9 g), melting point 227–228°C.

EXAMPLE 4

Compound H

A suspension of (±)-trans-2-(3,4-dichlorophenyl)-N-methyltetrahydrothiopyran-2-carbothioamide-1-oxide (2.0 g) in dry methylene chloride (70 ml) was treated with phosphorus pentasulphide (1.32 g) and stirred at room temperature for 2 hours. The mixture was filtered and the filtrate evaporated giving a colourless oil. The oil was purified by flash chromatography on silica, eluting with toluene to give colourless crystals (1.01 g). This solid was recrystallised from cyclohexane giving (±)-2-(3,4-dichlorophenyl)-N-methyltetrahydrothiopyran-2-carbothioamide (0.70 g) as colourless crystals, melting point 116°–117° C.

REFERENCE EXAMPLE 1

A solution of potassium tert-butoxide (5.26 g) in anhydrous tetrahydrofuran (20 ml) under argon was treated at 10°–15° C., during 20 minutes, with a solution of (±)-(4-chlorobutyl)sulphinylmethylbenzene (5.4 g) in anhydrous tetrahydrofuran (20 ml). Stirred at room temperature for 1 hour.

The reaction mixture was diluted with water (100 ml) and extracted with methylene chloride (3×50 ml). The combined extracts were washed with water (2×50 ml), dried over magnesium sulphate and evaporated (45° C./10 mmHg). The residual solid was dried (45° /8.4 mmHg) to give (±)-2-phenyltetrahydrothiopyran-1-oxide (mixture of cis/trans isomers), a colourless solid (4.11 g, 90%), melting point 118°–120° C.

By proceeding in a similar manner to that hereinbefore described above but replacing (±)-(4-chlorobutyl)sulphinylmethylbenzene by the appropriately substituted 1-[(4-chlorobutyl)sulphinylmethyl]benzene, there were prepared:

(±)-2-(4-chlorophenyl)tetrahydrothiopyran-1-oxide (mixture of cis-trans isomers), a colourless solid, melting point 116°–141° C., from (±)-4-chloro-1-[(4-chlorobutyl)sulphinylmethyl]benzene.

(±)-(2-(3-trifluoromethylphenyl)tetrahydrothiopyran-1-oxide (mixture of cis/trans isomers), a colourless solid, melting point 108°–119° C., after purification by flash chromatography on silica, eluting with ethyl acetate/ methanol : 9/1, from (±)-1-[(4-chlorobutyl)sulphinylmethyl]-3-trifluoromethylbenzene.

(±)-2-(2-naphthyl)tetrahydrothiopyran-1-oxide (mixture of cis/trans isomers), a colourless solid, melting point 131°–140° C., after being purified by flash chromatography on silica, eluting with ethyl acetate/methanol: 9/1 from (±)-2-[(4-chlorobutyl)sulphinylmethyl]naphthalene.
2-(3,4-dichlorophenyl)tetrahydrothiopyran-1-oxide (mixture of cis/trans isomers), a colourless solid, melting point 104°–106° C. , after being purified by flash chromatography on silica, eluting with ethyl acetate/ methanol: 95/5, from (±)-1-[(4-chlorobutyl)sulphinylmethyl]-3,4-dichlorobenzene.

(±)-2-(4-phenylphenyl)tetrahydrothiopyran-1-oxide (mixture of cis/trans isomers), a pale yellow solid, melting point 155°–158° C., from (±)-1-[(4-chlorobutyl)sulphinylmethyl]-4-phenylbenzene.

(±)-2-(3-cyanophenyl)tetrahydrothiopyran-1-oxide (mixture of cis/trans isomers), a colourless solid, melting point 116°–117° C., from (±)-3-cyano-1-[(4-chlorobutyl)sulphinylmethyl]benzene.

REFERENCE EXAMPLE 2

A solution of sodium hydroxide (1.60 g) in water (25 ml) was treated with benzylthiouronium chloride (8.51 g) and stirred at 70° C. for 20 minutes. The solution was cooled to 20° C., treated with a solution of sodium hydroxide (2.02 g) in water (5 ml) followed by 1-bromo- 4-chlorobutane (7.20 g). Stirred at room temperature for 18 hours.

The mixture was extracted with methylene chloride (2×100 ml). The extracts were washed with water, dried over magnesium sulphate and evaporated to give crude (4-chlorobutyl)thiomethylbenzene, a colourless oil (9.0 g).

A solution of this crude sulphide (9.0 g) in methylene chloride (88 ml) was treated dropwise during 2 hours at 2° C. with a solution of 85% m-chloroperbenzoic acid (9.02 g) in methylene chloride (88 ml). Stirred for 1 hour at 20° C. Treated with further 85% m-chloroperbenzoic acid (0.90 g) in methylenechloride (9 ml) and stirred at 20° C. for 18 hours.

The reaction mixture was washed with saturated sodium bicarbonate solution (3=35 ml) and saturated sodium chloride solution (3=35 ml). The organic phase was dried over magnesium sulphate and evaporated. The residual solid (9.6 g) was purified by flash chromatography on silica eluting with ethyl acetate/methanol:95/5 to give (±)-4-chlorobutyl)sulphinylmethylbenzene, a colourless solid (5.4 g, 56%), melting point 48°-50° C.

REFERENCE EXAMPLE 3

A solution of 4-chloro-1-[(4-chlorobutyl)thiomethyl]-benzene (5.0 g) in methylene chloride (50 ml) was treated dropwise during 1 hour, at 0° C., with a solution of m-chloroperbenzoic acid (3.45 g) in methylene chloride (50 ml).

The reaction mixture was washed with saturated sodium bicarbonate solution (3=50 ml) and saturated brine (3=50 ml), dried over magnesium sulphate and evaporated. The residual oil was purified by flash chromatography on silica, eluting with ethyl acetate/methanol:97.5/2.5 to give 4-chloro-1-[(4-chlorobutyl)sulphinylmethyl]- benzene, a colourless solid (4.42 g, 83%), melting point 56–58° C.

By proceeding in a similar manner to that hereinbefore described above but replacing 4-chloro-1-[(4-chlorobutyl)thiomethyl]benzene by the appropriately substituted 1-[(4-chlorobutyl)thiomethyl]benzene, there were prepared:

(±)-1-[(4-chlorobutyl)sulphinylmethyl]-3-trifluoromethylbenzene, a colourless oil, omitting the purification by flash chromatography, from 1-[(4-chlorobutyl)thiomethyl]-3-trifluoromethylbenzene.

(±)-2-[(4-chlorobutyl)sulphinylmethyl]naphthalene, a colourless solid, melting point 88°-90° C., after being purified by flash chromatography on silica, eluting with ethyl acetate/methanol: 95/5 to give from 2-[(4-chlorobutyl)thiomethyl]naphthalene.

(±)-1-[(4-chlorobutyl)sulphinylmethyl]-3,4-dichlorobenzene, a colourless solid, melting point 47°–49° C., omitting the purification by flash chromatography, from 1-[(4-chlorobutyl)thiomethyl]-3,4-dichlorobenzene.

(±)-1-[(4-chlorobutyl)sulphinylmethyl]-4-phenylbenzene, a colourless solid, melting point 121°-122° C., after being purified by flash chromatography on silica eluting with ethyl acetate/methanol: 95/5, from 1-[(4-chlorobutyl)thiomethyl]-4-phenylbenzene.

(±)-3-cyano-1-[(4-chlorobutyl)sulphinylmethyl]benzene as a colourless oil, after being purified by flash chromatography on silica, eluting with ethyl acetate/methanol: 95/5 to give from 3-cyano-1-[4-chlorobutyl)thiomethyl]benzene.

REFERENCE EXAMPLE 4

A solution of sodium hydroxide (2.0 g) in water (30 ml), under argon, was treated with 4-chlorobenzylthiouronium chloride (11.86 g) and stirred at 70° C. for 20 minutes. The phase transfer catalyst tris(3,6-dioxaheptyl)amine (TDA-1)(5 drops) was added and heating maintained at 70° C. for 2 hours. The mixture was cooled for 20° C. and treated with a solution of sodium hydroxide (2.4 g) in water (10 ml) followed by 1-bromo-4-chlorobutane (8.57 g). Stirred at room temperature for 18 h.

The reaction mixture was extracted with methylene chloride (3×75 ml). The combined extracts with water (2×50 ml), dried over magnesium sulphate and evaporated (45° C./10 mmHg) to give 4-chloro-1- [(4-chlorobutyl)thiomethyl]benzene, a colourless oil (11.03 g).

REFERENCE EXAMPLE 5

A solution of sodium (1.04 g) in anhydrous methanol (50 ml) was treated with 3-trifluoromethylbenzylmercaptan (8.7 g) and added dropwise during 30 minutes, at room temperature, under argon, to a solution of 1-bromo-4-chlorobutane (7.75 g) in anhydrous methanol (50 ml). Stirred at room temperature for 15 min.

The solution was evaporated in vacuo. The residue was treated with water (60 ml) and extracted with methylene chloride (3×25 ml). The combined extracts were dried over magnesium sulphate and evaporated to give 1-[(4-chlorobutyl)thiomethyl]-3-trifluoromethylbenzene, a pale yellow oil, (12.4 g, 97%).

By proceeding in a similar manner to that hereinbefore described above but replacing 3-trifluoromethylbenzylmercaptan by the appropriate mercaptan, there were prepared:

2-[(4-chlorobutyl)thiomethyl]naphthalene, a colourless solid, from 2-naphthylmethylthiol.

1-[(4-chlorobutyl)thiomethyl]-3,4-dichlorobenzene, a pale yellow oil, from 3,4-dichlorobenzylmercaptan.

1-[(4-chlorobutyl)thiomethyl]-4-phenylbenzene, a yellow oil, from 4-phenylbenzylmercaptan.

REFERENCE EXAMPLE 6

α-Bromo-m-toluonitrile (50 g) and thiourea (22.8 g) were heated at reflux in ethanol (300 ml) for 1.5 hours. After cooling in ice the thiouronium salt was collected (60 g).

The thiouronium salt was suspended in water (250 ml) and treated with sodium hydroxide (18 g) and stirred at 70° C. for 1 hour. The almost clear solution was cooled to room temperature and 1-bromo-4-chlorobutane (37.7 g) added and the mixture stirred for 18 h. The mixture was extracted with dichloromethane (3×100 ml). The organic extracts were combined, dried over magnesium sulphate, filtered and evaporated to give 3-cyano-1-[(4-chlorobutyl)thiomethyl]benzene (52 g) as a light yellow oil.

EXAMPLE 5

Compound I

A suspension of (±)-trans-2-(3-cyanophenyl)-N-methyltetrahydrothiopyran-2-carbothioamide-1-oxide (1 g), 0.0034M) in 1N aqueous sodium hydroxide solution (4 ml) was warmed overnight with stirring at 80° C. The suspension was cooled, neutralised with 2N hydrochloric acid and the white solid collected to give (±)-trans-2-(3-carbamoylphenyl)-N-methyltetrahydrothiopyran-2-carbothioamide-1-oxide 0.8 g, melting point 225°-226° C.

Elemental analysis: $C_{14}H_{18}N_2O_2S_2$ requires C, 54.2; H, 5.8; N, 9.0; S, 20.6%. Found : C, 54.2; H, 5.9; N, 87.; S, 21.0%.

EXAMPLE 6

Compound J

To 135 cc of a 1.6M solution of n-butyllithium in hexane maintained in an atmosphere of argon at a temperature of about −60° C., add, dropwise, over 10 minutes, a solution of 22 g of di-isopropylamine in 125 cc of a mixture of anhydrous hexamethylphosphoric triamide and anhydrous tetrahydrofuran (47:53 v/v) and stir the mixture for 5 minutes. Then add, dropwise, over 20 minutes, a solution of 28 g of 2-phenyltetrahydrothiophene in 125 cc of the mixture of anhydrous hexamethylphosphoric triamide and anhydrous tetrahydrofuran (47:53 v/v) and stir the mixture for 10 minutes. Then add, dropwise, over 15 minutes, a solution of 18.3 of methyl isothiocyanate in 62 cc of the mixture of anhydrous hexamethylphosphoric triamide and anhydrous tetrahydrofuran (47:53 v/v), stirring the mixture at the same temperature initially for 45 minutes, then for 1 hour, allowing the temperature to increase progressively to +15° C. Lastly, add 600 cc of distilled water and 600 cc of ethyl acetate. After separation, the organic phase is washed successively with 600 cc of distilled water, 250 cc of an aqueous solution of $\underline{N}$ hydrochloric acid, twice with 600 cc (1200 cc in total) of distilled water, then dried over anhydrous sodium sulphate, filtered and concentrated to dryness under reduced pressure (15 mm Hg; 2 kPa) at 45° C. The product obtained (37.5 g) is dissolved in 100 cc of boiling ethanol and activated charcoal is added to the solution thus obtained; the solution is then filtered, cooled and set aside for 2 hours at a temperature of about 20° C. The crystals formed are separated by filtration, washed with 15 cc of ethanol, then twice with 20 cc (40 cc in total) of di-isopropyl oxide and dried under reduced pressure (15 mm Hg; 2 kPa) at 20° C. The product obtained (17.7 g) is mixed with 1.3 g of the same product prepared beforehand under the same conditions, then dissolved in 70 cc of boiling ethanol. Activated charcoal is added to the solution thus obtained; the solution is then filtered while hot, cooled and set aside for 1 hour at a temperature of about 5° C. The crystals formed are separated by filtration, washed with 10 cc of ethanol and twice with 10 cc (20 cc in total) of di-isopropyl oxide and dried under reduced pressure (1 mm Hg; 0.13 kPa) at 53° C. 15.5 g of N-methyl-2-phenyltetrahydrothiophene-2-carbothioamide, with a melting point of 113° C, is thus obtained.

EXAMPLE 7

Compound K

To 97.5 cc of a 1.6M solution of n-butyllithium in hexane maintained in an atmosphere of argon at a temperature of about −60° C., add, dropwise, over 15 minutes, a solution of 16 g of di-isopropylamine in 90 cc of a mixture of anhydrous hexamethylphosphoric triamide and anhydrous tetrahydrofuran (47:53 v/v) and stir the mixture for 10 minutes. Then add, dropwise, over 15 minutes, a solution of 22.5 g of 2-phenyltetrahydrothiophene-1-oxide in 90 cc of the mixture of anhydrous hexamethylphosphoric triamide and anhydrous tetrahydrofuran (47:53 v/v) and continue to stir the mixture for 20 minutes. Then add, dropwise, over 15 minutes, a solution of 13.6 g of methyl isothiocyanate in 55 cc of the mixture of anhydrous hexamethylphosphoric triamide and anhydrous tetrahydrofuran (47:53 v/v) and continue to stir the mixture for 2 hours, allowing the temperature to increase progressively to 20° C. The reaction mixture is taken up with 450 cc of distilled water and 225 cc of ethyl acetate. The crystals formed are separated by filtration, washed twice with 30 cc (60 cc in total) of ethyl acetate, with 30 cc of di-isopropyl oxide and dried under reduced pressure (15 mm Hg; 2 kPa) at 20° C. A first batch of 16.3 g is thus obtained. The filtrate is separated and the organic phase is washed three times with 50 cc (150 cc in total) of distilled water, dried over anhydrous sodium sulphate, filtered and concentrated to dryness under reduced pressure (15 mm Hg; 2kPa) at 50° C. 30 cc of ethyl acetate is added to the product obtained and the crystals formed are separated by filtration, washed twice with 5 cc (10 cc in total) of di-isopropyl oxide and dried under reduced pressure (15 mm Hg; 2 kPa) at 20° C. A second batch of 1 g is thus obtained. Both batches (17.3 g) are mixed with 0.7 g of the same product, prepared beforehand under the same conditions and dissolved in 500 cc of boiling ethanol. Activated charcoal is added to the solution thus obtained; the solution is filtered while hot, cooled, then set aside for 15 hours at a temperature of about 5° C. The crystals formed are separated by filtration, washed with 20 cc of ethanol, then twice with 25 cc (50 cc in total) of di-isopropyl oxide and dried under reduced pressure (1 mm Hg; 0.13 kPa) at 50° C. 15 g of N-methyl-2-phenyltetrahydrothiophene-2-carbothioamide-1-oxide, with a melting point of 236° C., is thus obtained.

2-Phenyltetrahydrothiophene-1-oxide can be prepared as follows: to a solution of 25.4 g of 2-phenyltetrahydrothiophene in 1550 cc of methylene chloride maintained at a temperature of about 20° C. add, dropwise, over 45 minutes, a solution of 31.8 g of meta-chloroperbenzoic acid 85 % in 630 cc of methylene chloride. Stir the mixture for 18 hours at the same temperature, then add, dropwise, a solution of 15.5 g of sodium hydrogen carbonate in 150 cc of water and stir until no more gas is given off. The mixture is then separated; the organic phase is washed three times with 100 cc (300 cc in total) of distilled water, dried over anhydrous sodium sulphate, filtered and concentrated under reduced pressure (15 mm Hg; 2 kPa) at 80° C. The product obtained (32 g) is distilled under reduced pressure (0.3 mm Hg; 0.04 kPa). 20 g of 2-phenyltetrahydrothiophene-1-oxide distilling at 136°-138° C. is thus obtained.

EXAMPLE 8

Compounds L and M

By proceeding in a similar manner to Example 2, there were prepared (±)-trans-2-(3-fluorophenyl)-N-methyltetrahydrothiopyran-2-carbothioamide-1-oxide, a colourless solid, melting point 228° C. (with decomposition), after being purified by trituration with acetone, from (±)-2-(3-fluorophenyl)tetrahydrothiopyran-1-oxide (mixture of cis/trans isomers);

(±)-trans-2-(3,5-dichlorophenyl)-N-methyltetrahydrothiopyran-2-carbothioamide-1-oxide, a colourless solid, melting point 235°–237° C., after being purified by recrystallisation from ethanol, from (±)-2-(3,5-dichlorophenyl)tetrahydrothiopyran-1-oxide (mixture of cis/trans isomers).

REFERENCE EXAMPLE 7

By proceeding in a similar manner to Reference Example 1 there were prepared (±)-2-(3-fluorophenyl)tetrahydrothiopyran-1-oxide (mixture of cis/trans isomers), a colourless solid, melting point 95°–98° C., after purification by trituration from petroleum ether (b.p. 60°–80° C.), from (±)-1-[(4-chlorobutyl)sulphinylmethyl]-3-fluorobenzene;

(±)-2-(3,5-dichlororophenyl)tetrahydrothiopyran-1-oxide (mixture of cis/trans isomers), a colourless solid, melting point 122°–124° C., after purification by trituration from diethyl ether, from (±)-1-[(4-chlorobutyl)sulphinylmethyl]-3,5-dichlorobenzene.

REFERENCE EXAMPLE 8

By proceeding in a similar manner to Reference Example 3 there were prepared (±)-1(4-chlorobutyl)sulphinylmethyl]3-fluorobenzene, a colourless solid, melting point 39°–40° C., after being purified by flash chromatography on silica, eluting with ethyl acetate/methanol:99/1, from 1-[(4-chlorobutyl)thiomethyl]-3-fluorobenzene;

(±)-1-[(4-chlorobutyl)sulphinylmethyl]-3,5-dichlorobenzene, after being purified by flash chromatography on silica, eluting with ethyl acetate/methanol: 99/1, from 1-[(4-chlorobutyl)thiomethyl]-3,5-dichlorobenzene.

REFERENCE EXAMPLE 9

By proceeding in a similar manner to Reference Example 5 there were prepared

1-[(4-chlorobutyl)thiomethyl]-3-fluorobenzene, a yellow oil, from 3-fluorobenzylmercaptan;

[(4-chlorobutyl)thiomethyl]-3,5-dichlorobenzene, a yellow oil from 3,5-dichlorobenzylmercaptan.

The present invention includes within its scope pharmaceutical compositions which comprise a compound of general formula (I), a pharmaceutically acceptable bioprecursor thereof or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I), a pharmaceutically acceptable bioprecursor thereof or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from 0.001 to 50 mg/kg body weight per day by oral administration. By inhalation, either as a nebulised solution or as a formulated dry powder, the preferred daily dosage is from 0.001 to 5 mg/kg body weight.

The following Example illustrates pharmaceutical compositions according to the present invention.

COMPOSITION EXAMPLE

No. 2 size gelatin capsules each containing:

| | |
|---|---|
| (±)-trans-N-methyl-2-phenyltetrahydrothiopyran-2-carbothioamide-1-oxide | 20 mg |
| lactose | 100 mg |
| starch | 60 mg |
| dextrin | 40 mg |
| magnesium stearate | 1 mg | were prepared in accordance with the usual procedure.

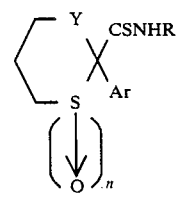

-continued

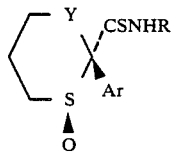

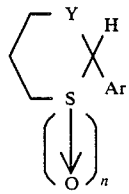

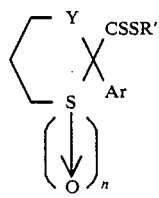

We claim:
1. A thioformamide derivative of the formula:

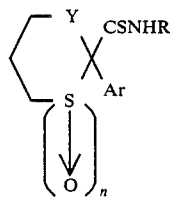

wherein R represents a straight- or branched-chain alkyl radical containing from 1 to 4 carbon atoms, Ar represents a phenyl group unsubstituted or substituted in the 3- and/or 5-position with an electron-withdrawing group selected from a cyano, nitro, trifluoromethyl, carbamoyl, carboxy, $C_{2-5}$-alkanoyl, $C_{2-5}$-alkoxycarbonyl or $C_{1-4}$-alkylsulphonyl group or a fluorine, chlorine or bromine atom, and optionally further substituted on the phenyl group with halogen atom(s), $C_{1-4}$-alkyl or phenyl group(s) or the group Ar may be substituted with halogen atom(s), $C_{1-4}$-alkyl or phenyl group(s) or with substituents which together form a naphthyl ring, Y represents an ethylene or methylene radical or a valency bond, and n represents 0 or 1, or a pharmaceutically acceptable salt thereof.

2. A compound according to claim 1 wherein Y represents a methylene radical.
3. A compound according to claim 1 wherein n is 1.
4. A compound according to claim 1 wherein Ar represents the phenyl, 4-chlorophenyl, 4-phenylphenyl, 3-trifluoromethylphenyl, 3-fluorophenyl, 3-cyanophenyl, 3-carbamoylphenyl, 3,4-dichlorophenyl, 3,5-dichlorophenyl or 2-naphthyl group.
5. A compound according to claim 1 wherein R is methyl.
6. A compound according to claim 1 wherein n is 1 and the oxygen atom of the sulphoxide group is in the trans position relative to the group —CSNHR, wherein R is as defined in claim 1.
7. A compound according to claim 1 which is (±)-trans-N-methyl-2-phenyltetrahydrothiopyran-2-carbothioamide-1-oxide, (±)-trans-2-(4-chlorophenyl)-N-methyltetrahydrothiopyran-2carbothioamide-1-oxide, (±) -trans-N-methyl-2-(3-trifluoromethylphenyl)tetrahydrothiopyran-2-carbothioamide-1-oxide, (±)-trans-N-methyl-2-(2-naphthyl)tetrahydrothiopyran-2-carbothioamide-1-oxide, (±)-trans-2-(3,4-dichlorophenyl)-N-methyl-tetrahydrothiopyran-b 2-carbothioamide-1-oxide, (±)-trans-N-methyl-2(4-phenylphenyl)tetrahydrothiopyran-2-carbothioamide-1-oxide, (±)-trans-2-(3-cyanophenyl)-N-methyltetrahydrothiopyran-2-carbothioamide-1-oxide, (±)-2-(3,4-dichlorophenyl)-N-methyltetrahydrothiopyran-2-carbothioamide, (±)-trans-2-(3-carbamoylphenyl)-N-methyltetrahydrothiopyran-2-carbothioamide-1-oxide, (±)-N-methyl-2-phenyltetrahydrothiophene-2-carbothioamide, (±)-N-methyl-2-phenyltetrahydrothiophene-2-carbothioamide-1-oxide, (±)-trans-2-(3-fluorophenyl)-N-methyltetrahydrothiopyran-2-carbothioamide-1-oxide, or (±)-trans2-(3,5-dichlorophenyl)-N-methyltetrahydrothiopyran-2-carbothioamide-1-oxide or a pharmaceutically acceptable salt thereof.

8. A pharmaceutical composition useful in the treatment of disorders associated with vascular smooth muscle contraction, respiratory smooth muscle contraction and contraction of smooth muscle of gastro-intestinal tract, urinary bladder and uterus which comprises a therapeutically effective amount of a thioformamide derivative of formula (I) as defined in claim 1 or a pharmaceutically acceptable salt thereof in association with a pharmaceutically acceptable carrier or coating.

* * * * *